(12) United States Patent
Sen et al.

(10) Patent No.: US 6,738,655 B1
(45) Date of Patent: May 18, 2004

(54) ENDOMYOCARDIAL MONOPHASIC ACTION POTENTIAL FOR EARLY DETECTION OF MYOCARDIUM PATHOLOGY

(75) Inventors: Luyi Sen, Stevenson Ranch, CA (US); Guanggen Cui, Stevenson Ranch, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/958,452

(22) PCT Filed: Apr. 4, 2000

(86) PCT No.: PCT/US00/09104
§ 371 (c)(1),
(2), (4) Date: Oct. 3, 2001

(87) PCT Pub. No.: WO00/59375
PCT Pub. Date: Oct. 12, 2000

Related U.S. Application Data
(60) Provisional application No. 60/128,181, filed on Apr. 5, 1999.

(51) Int. Cl.[7] .................................................. A61B 5/04
(52) U.S. Cl. ........................ 600/374; 600/509; 607/122
(58) Field of Search ................................. 600/509, 523, 600/373, 374, 375; 607/119, 122

(56) References Cited

U.S. PATENT DOCUMENTS 4,699,147 A * 10/1987 Chilson et al. ............. 128/642
5,681,308 A * 10/1997 Edwards et al. ............... 606/41
5,772,590 A * 6/1998 Webster, Jr. .................. 600/374
6,014,579 A * 1/2000 Pomeranz et al. ........... 600/374

FOREIGN PATENT DOCUMENTS

EP          0 682 911 A1 *  5/1995   ........... A61B/5/042
WO         WO 99/05971    *  2/1999   ............ A61B/8/08

* cited by examiner

Primary Examiner—Carl Layno
(74) Attorney, Agent, or Firm—David L. Dawes; Myers Dawes Andras & Sherman LLP

(57) ABSTRACT

A catheter-delivered electrode array is used to three dimensionally map the endomyocardial monophasic action potential (MAP). The catheter is used in a method for endomyocardial MAP mapping and for establishing diagnostic criteria for the cardiac myocyte injury. During allograft rejection, conduction impairment occurs within the atrial myocardium. Abnormalities of the terminal force of the P wave in Lead V1 (ptfV1) and dispersion of corrected atrial repolarization (Ta-TcD) represent interatrial conduction defects that accompanies the rejection process. Three dimensional endomyocardium monophasic action potential mappings are used to directly monitor the pathophysiological changes in cardiac myocytes. Changes in amplitude, duration and morphology of the action potential were recorded and used to detect the early rejection of the transplant organ with high sensitivity and specificity. Using this MAP-mapping system, the area of myocardium injury induced by a coronary artery occlusion or by ablation can be pin pointed.

10 Claims, 11 Drawing Sheets

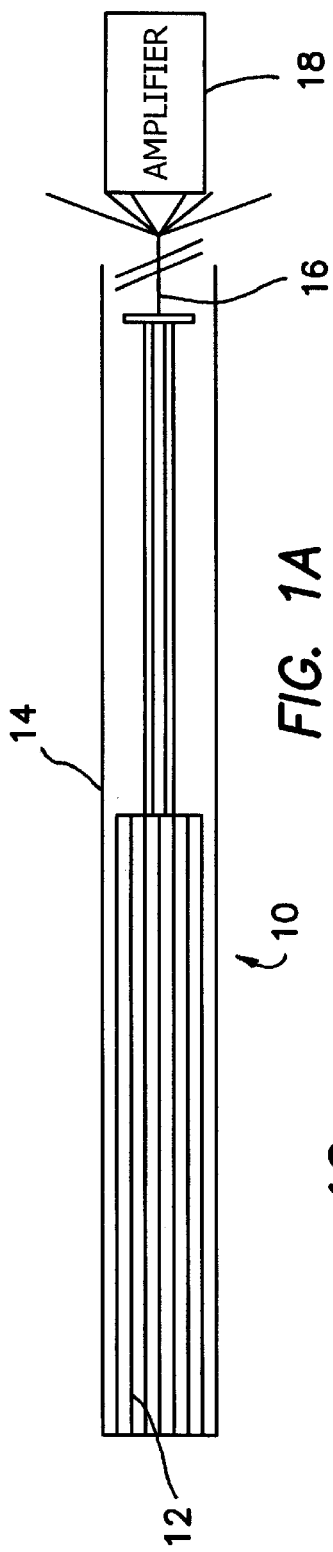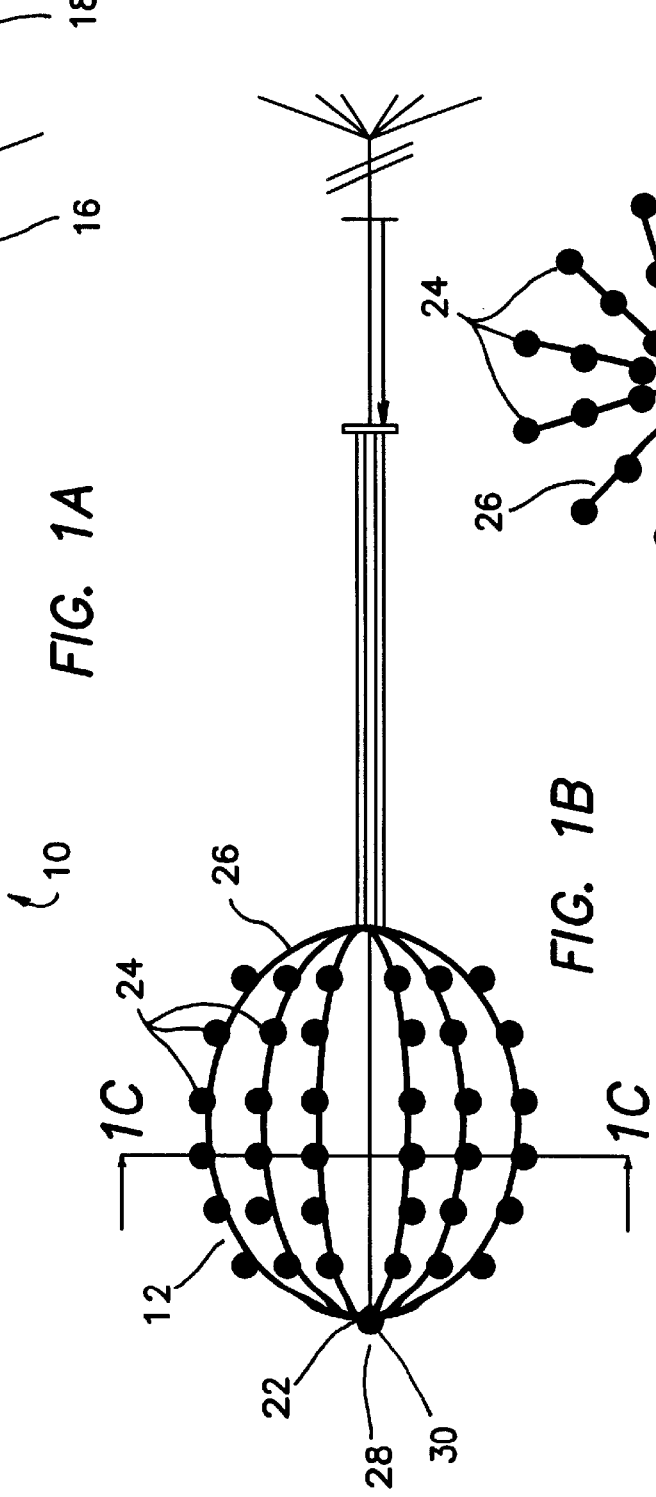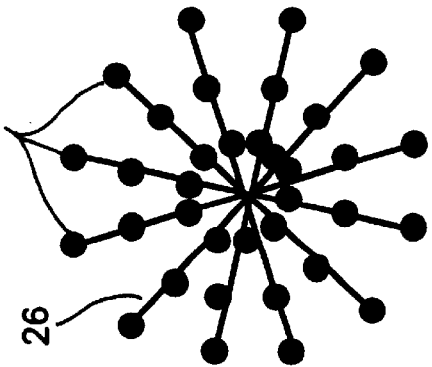
FIG. 1A
FIG. 1B
FIG. 1C

ENDOMYOCARDIAL MONOPHASIC ACTION POTENTIAL FOR EARLY DETECTION OF MYOCARDIUM PATHOLOGY

RELATED APPLICATIONS

The application is related to U.S. Provisional Patent Application serial No. 60/128,181, filed on Apr. 5, 1999, which is incorporated herein by reference.

BACKGROUND OF THE INVENTION

1. Field of the Invention

The invention relates to the field of electrocardiology and in particular to a method and apparatus for endomyocardial monophasic action potential for early detection of myocardium pathology.

2. Description of the Prior Art

Electrocardiography (ECG) has been used for clinical diagnosis since end of last century. The concept of ECG is that the properties of electrical flow or conductance of the heart is reflected by the body surface electrical signal change. However, it is subject to a number of well known limitations, which arise mainly due to the indirect nature of the measurement. Using microelectronics to directly measure the transmembrane action potential has been practices on the isolated bundles of cardiac fibers or cardiac myocytes in the basic research laboratory for several decades. The changes in the amplitude, time course and the morphology of the action potential characteristically represent the electrophysiology of the cardiac myocytes. Directly measuring the monophasic action potential of the cluster of the myocytes in the endomyocardium using a monophasic action potential (MAP) catheter has been introduced in clinical electrophysiologic testing for more than two decades. Although direct measurement could record the changes of the electrophysiological function of cell membrane in several cardiac myocytes measured in a local region of about 1 mm diameter area, it could not represent the pathophysiological changes in whole heart. The measurement area can not be increased, because too many cells would need to be measured by one electrode. The electrical signal from each cell will interact each other cell to cause a false reading.

To avoid these problems, the prior art solution was to place the electrode in several areas and measure the MAP one by one. This is extremely time consuming, and it is hard to tell the precise position of each of the measurements. Therefore, manual point-to-point measurement is not practical clinically. Also known are electrical signal mappin "sock" and "carpet" techniques used to map the electrical signals in the epicardium, which is not MAP, for isolated heart preparation and open chest preparation in experimental laboratories. The use of a basket or "lantern" shape for contact measurements with the endomyocardium has also been attempted by Boston Scientific in a device marketed under the trademark, Constellation catheter. Although the significance was not appreciated, known or practiced in the prior art, the Constellation catheter does not have Ag/AgCl electrodes and the structure of the basket is too soft or limp to obtain good electric contact with the endomyocardium. Consequently, the Constellation catheter is incapable of sensing or recording the MAP and can only record general electrical signals, which have no material diagnostic significance or uniqueness.

BRIEF SUMMARY OF THE INVENTION

The invention is an apparatus for three-dimensional mapping of endomyocardial monophasic action potential (MAP) of endomycardial tissue. The invention comprises a catheter with a distal and proximal end. A wire basket is disposed on the distal end of the catheter. A plurality of electrodes is carried by the basket. The basket is self-expandable by reason of resiliency of the basket to a size and stiffness sufficient to cause the electrodes to make intimate contact with the endomycardial tissue. A flexible cable or other means of electrical communication is disposed in the catheter electrically coupling the plurality of electrodes to the proximal end of the catheter. The flexible cable is comprised of a plurality of flexible wires with one wire being provided to each electrode.

The plurality of electrodes is provided with a Ag/AgCl plating. The number of the electrodes carried by the basket is preferably at least 64. The number of support wires defining the basket is preferably at least 8 and each support wire has at least 8 electrodes. Thin electrical wires carried by the support wires may be connected individually to each of the electrodes or the electrodes may be electrically coupled to each other in different sets. The electrodes are preferably equally or uniformly distributed or arranged on the basket. The basket wires and electrode are insulated. It is to be expressly understood that fewer or more electrodes than 64 are also within the scope of the invention and that the arrangemenit of their mutual connection is arbitrary.

The apparatus further comprises a sheath. The sheath is temporarily disposed over the basket to retain the basket in a collapsed configuration. The sheath is telescopically removable from the basket to allow the basket to self-expand.

The apparatus further comprises an electrophysiological analyzer coupled to the cable to record data from each of the plurality of electrodes and to analyze the data to generate a three-dimensional endomyocardium mapping of endomyocardial monophasic action potential from the plurality of electrodes.

The invention is also defined as a method of determining the myocardium injury lelectrical-pathophysiology of cardiac myocytes. The method comprises the steps of providing a catheter as described above, namely a catheter having with a distal and proximal end, and a wire basket disposed on the distal end of the catheter with a plurality of Ag/AgCl plated electrodes carried by the basket, having a flexible cable disposed in the catheter electrically coupling the plurality of electrodes to the proximal end of the catheter, and a sheath temporarily disposed over the basket to retain the basket in a collapsed configuration. The catheter is disposed into a heart chamber to be mapped. The sheath is telescopically removed from the basket to allow the basket to self-expand in the heart chamber. The basket is self-expandable by reason of resiliency of the basket to a size and stiffness sufficient to cause the electrodes to make intimate contact with the endomyocardial tissue. A heart data signal from each of the plurality of electrodes is recorded and electrophysiologically analyzed to generate a three-dimensional endomyocardium mapping of endomyocardial monophasic action potential from the plurality of electrodes.

In the illustrated embodiment the changes in ptf-V1 and/or the dispersion of Ta-Tc in the body surface 12-lead-electrocardiograms (ECG) is analyzed to determine atrial conduction disturbance associated with myocardium injury. If the ptf-V1 signal equals or exceeds 0.04 or the Ta-TcD signal equals or exceeds $0.06 \ s^{1/2}$ or both, then a determination is made that there is very likely some myocardium injury or dysfunction, in particular rejection of a heart transplant. The data signal, such as the ptf-V1 and/or Ta-TcD signal, is correlated to an the severity of the cardiac allograft rejection grade.

Accordingly, the endomyocardium monophasic action potential was measured using conventional single electrode MAP catheter in a rabbit heart transplant model. The characteristic changes in amplitude, duration and morphology of the action potential were observed to be able to detect the early rejection with high sensitivity and specificity. The three-dimensional MAP-mapping was able to pin point the area of the myocardium injury induced by a coronary artery occlusion or ablation.

The invention is better visualized by turning to the following drawings wherein like elements are referenced by like numerals.

BRIEF DESCRIPTION OF THE DRAWINGS

FIG. 1a is a diagrammatic side cross-sectional view of the catheter of the invention.

FIG. 1b is a side elevational view of the deployed configuration of the catheter of FIG. 1a.

FIG. 1c is a front elevational view of the deployed configuration of the catheter of FIG. 1a.

Figure 2A:
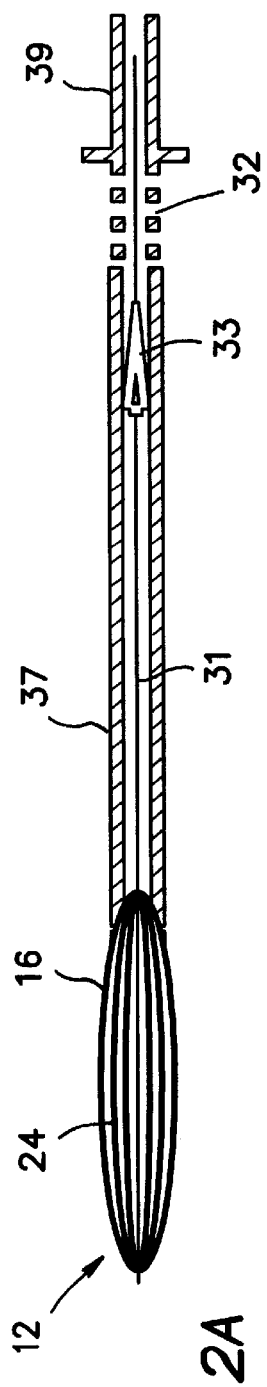
FIG. 2a is a side cross-sectional diagram of the catheter of the invention shown in a collapsed configuration.

The invention and its operability is better understood by now turning to the following detailed description of the preferred embodiments.

DETAILED DESCRIPTION OF THE PREFERRED EMBODIMENTS

The invention is directed to an apparatus and a methodology for three-dimensional mapping of endomyocardial monophasic action potential (MAP). A "lantern catheter" devised according to the invention is used for transpercutaneous catheterization followed by three dimensionally mapping the endomyocardial MAP. Preferably at least 64 points of MAP are recorded simultaneously and the data is analyzed by a conventional electrophysiological (EP) analysis system. It is to be expressly understood that the number and location of points mapped may be altered from what is expressly discussed in the illustrated embodiments without departing from the scope of the invention.

The invention is comprised of three components:
1) the use of three-dimensional mapping of the endomyocardium MAP to determine the myocardium injury/electrical-pathophysiology of cardiac myocytes induced by cardiac rejection, ischemia, inflammation and the like;
2) a technology and design of the lantern catheter for endomyocardial MAP mapping; and
3) a diagnostic criteria for the cardiac myocyte injury.

The "lantern" catheter, generally denoted by reference numeral 10, allows simultaneous, three-dimensional mapping of the entire endomyocardium MAP. Catheter 10 as shown in the diagrammatic side view of FIG. 1a is retained within a protection sheath 14 which retains basket 12 in a collapsed condition. Basket 12 is connected to a catheter lead 20 through which insulated copper wires 16 are disposed. Wires 16 are connected to electrodes 24 in basket 12 as discussed below at their distal ends and to a multichannel amplifier or multiplexer and other appropriate electronics 18 at its proximal end. Central trunk 31 of the catheter supports all of the wires 16 as diagrammatically shown in FIGS. 2a and 2b. Wires 16 are insulated or nonconducting so that they function as mechanical supports for electrodes 24. A plurality of very fine wires 41 are electrically coupled to corresponding electrodes 24 as diagrammatically depicted in FIG. 2c, which are therefore selectively and individually accessible for detection and recording through electronics 18.

Figure 2B:
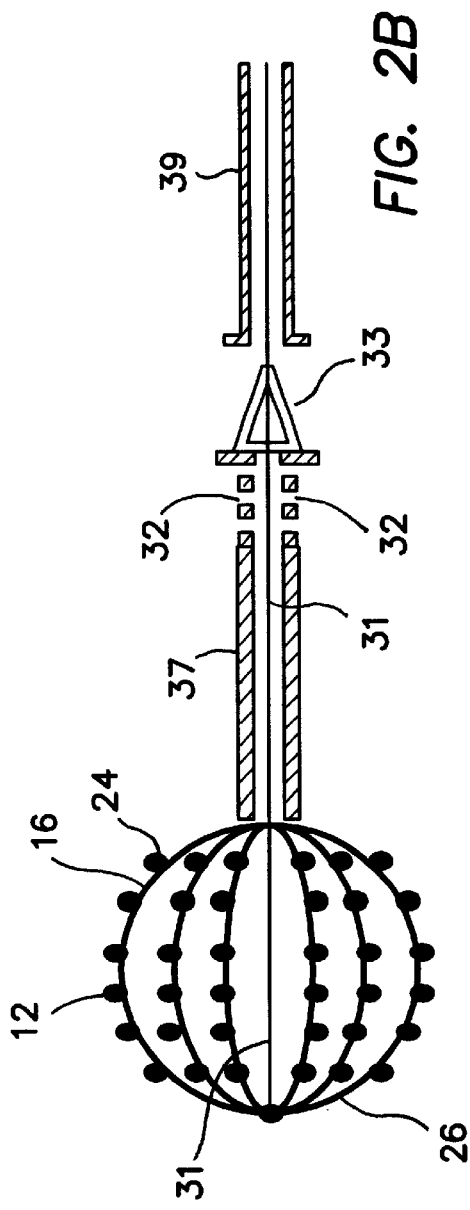
FIG. 2b is a side cross-sectional diagram of the catheter of the invention shown in an expanded or deployed configuration.
Figure 2C:
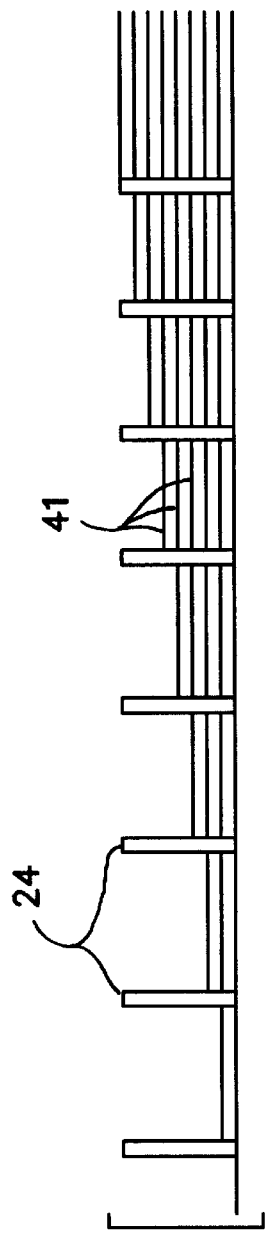
FIG. 2c is a diagrammatic depiction of the connection of the electrodes in a basket to their corresponding signal wires.

A hollow cylindrical shaft 37 is telescopically movable on central trunk 31 to open and close basket 12. A lock 33 disposed on central trunk 31 is provided to fix basket 12 in its open position while in the heart chamber and while being used to make the MAP mapping or recording. Lock 33 is disposed within shaft 37 as shown in FIG. 2a when basket 12 is in its collapsed configuration. Catheter 39 is advanced over central trunk 31, moving shaft 37 to the left in the illustration of FIG. 2a, thereby causing basket 12 to expand as shown in FIG. 2b. When shaft 31 and spring 32 are forced over lock 33, lock 33 is freed and snaps open by reason of its inherent resiliency to then provide a mechanical stop for the proximal end of spring 32. Lock 33 can be released by insertion into catheter 39 by advancing catheter 39 over lock 33 and reinserting lock 33 into spring 32 and/or shaft 37. This will then allow basket 12 to collapse and be withdrawn from the heart chamber. Spring 32 abuts the proximal end of shaft 37 to give basket 12 some flexibility during heart contractions and relaxations during each beat, i.e. basket 12 can be partially compressed and re-expanded by the surrounding beating heart walls while electrodes 24 maintain continuous and firm contact with the heart tissue. Electrodes 24 are spherical or rounded and sized to extend from wires 16 and thereby to provide positive and firm contact with the surrounding heart tissue. This feature in combination with the resilient nature of the basket/spring combination insure continuous and firm or intimate contact between electrodes 24 and the heart tissue, which contact is important to obtain valid readings.

Figure 3A:
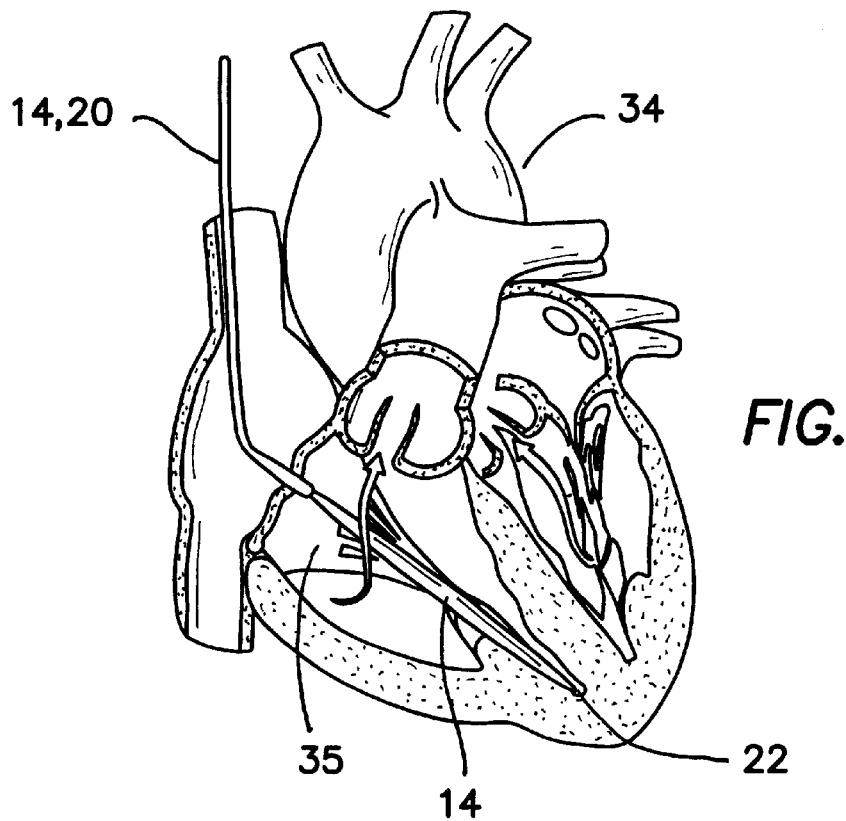
FIG. 3a is a side cross-sectional view of the catheter of the invention being disposed in the ventricle of a human heart.
Figure 3B:
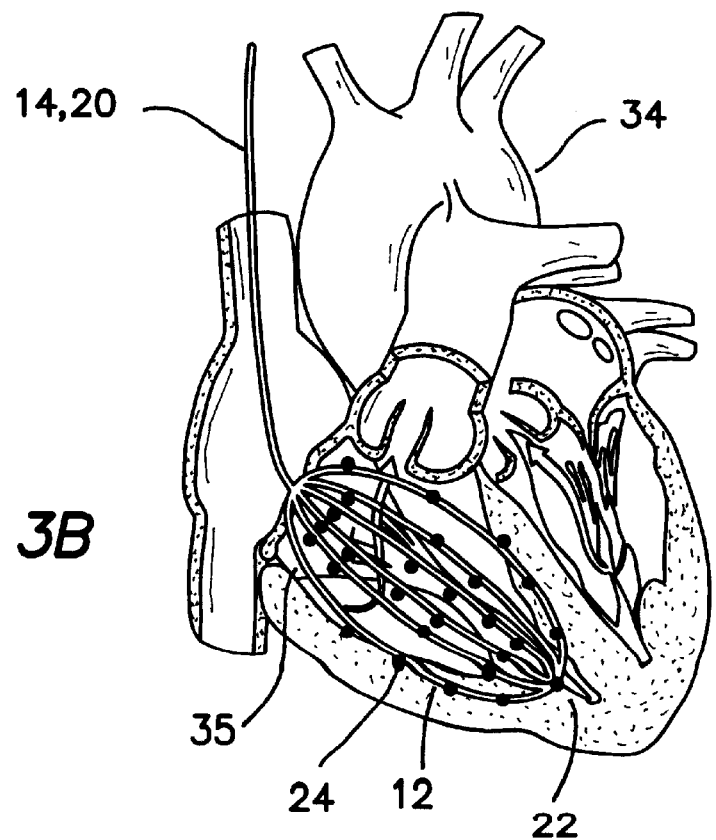
FIG. 3b is a side cross-sectional view of the catheter of the invention being deployed in the ventricle of a human heart.
Figure 4A:
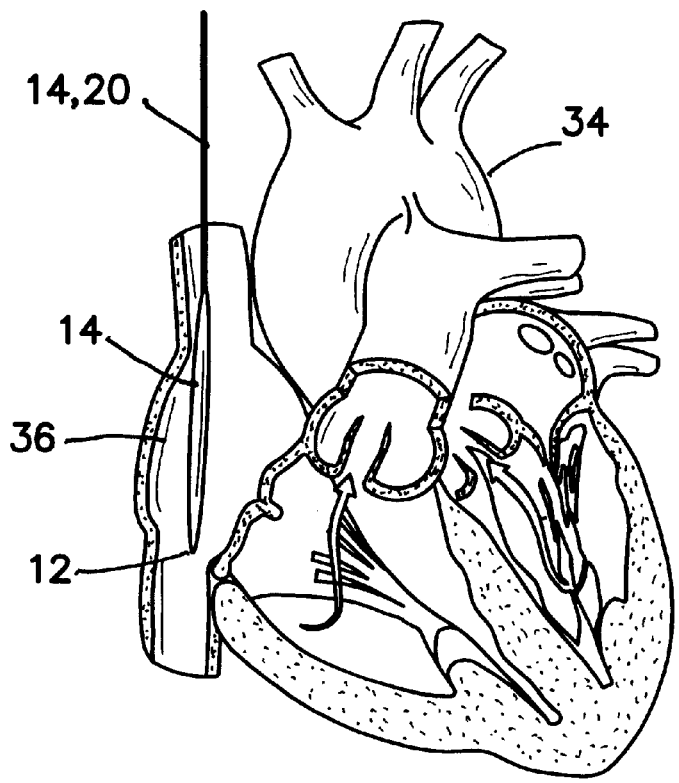
FIG. 4a is a side cross-sectional view of the catheter of the invention being disposed in the atrium of a human heart.
Figure 4B:
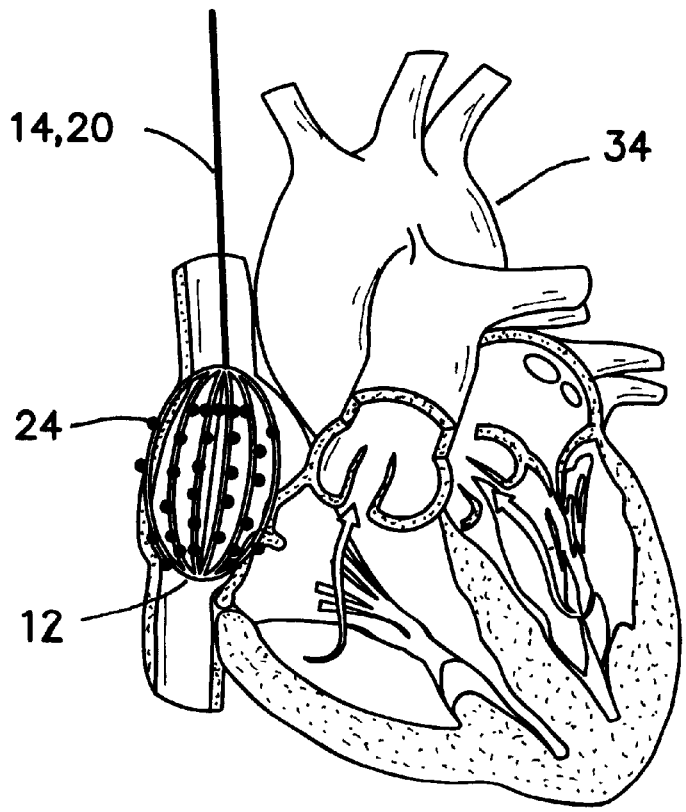
FIG. 4b is a side cross-sectional view of the catheter of the invention being deployed in the atrium of a human heart.

Catheter 10 is inserted in to a vein or artery percutaneously, then placed in to the right atrium 36 of heart 33 as shown in the side cross-sectional view of FIGS. 4a and 4b, or right ventricle or left ventricle 34 as shown in the side cross-sectional view of FIGS. 3a and 3b to map either atrial MAP or ventricular MAP as required. As diagrammatically shown in FIG. 4b and 3b respectively, after catheter 10 is placed into atrium 36 or ventricular chamber 35, and tip 22 of catheter 10 reaches the most distal part of the endomyocardium, sheath 14 of catheter 10 is telescopically withdrawn or advanced to open basket 12 of "lantern" 28 as shown in isolation in FIG. 1b, in ventricle 34 in FIG. 3b and in atrium 36 in FIG. 4b until all of the electrodes 24, which preferably is at least 64 points, contact the endomyocardium. Tip 22 of basket 12 may be provided with a radioopaque platinum or gold marker 30 to aid in its fluoroscopic detection and visualization, since stainless steel wires 26 and electrodes 24 can be very fine or small and difficult to unambiguously show in a fluoroscopic image. The "lantern" 28 shall collectively denote basket 12 of wires 26 and electrodes 24. Each electrode 24 is preferably made of or plated with Ag/AgCl. Wires 26 are preferably made from stainless steel, which provides the needed degree of resiliency and flexibility. Other alloy choices, gauges and material choices could be made for wires 26 consistent with the teachings of the invention.

The skeleton or wire 26 of lantern 28 is stiff or resilient enough so that when deployed from catheter 10 it resiliently expands as shown in front elevational view in FIG. 1c and intimately or tightly contacts the endomyocardium to make a good, or low resistance and low capacitance electrical contact with the cell membrane of the tissues to effectively be able to record the MAP of the endomyocardium and not be blinded or swamped by signals relating to the blood flow or heart muscles. The MAP from each electrode 24 is recorded simultaneously for any given time frame, typically from 5 to 10 min. Thus in the case that 64 electrodes are used, wires 16 also comprise a bundle of 64 wires or communication channels. The amplitude, time rate of change of the voltage, dV/dt, and duration of each MAP can be analyzed using Proka EP analysis system 18 manufactured by Pruka Engineering Inc. or other commercially available systems.

Early Diagnosis For Cardiac Rejection:

The illustrated use of catheter 10 is to detect the rejection of the heart transplantation at an early stage. The change of the action potential of the cell membrane occurs well in advance of any morphological change which could be observed in cardiac myocytes. In cardiac rejection, the autoimmuno reaction induced cellular dysfunction is first manifested in the alterations of cell membrane action potential. The changes of the amplitude and the duration of the MAP are the earliest signs of the cell injury.

Diagnosis Of Subendocardium Infarction:

Subendocardial infarction is the ischemic coronary artery disease induced myocardial infarction which is only localized in the subendocardium nontransmural. The diagnosis is difficult, because the ECG does not show the typical QRS change. The diagnosis criteria for the subendocardial infarction is ST or T changes that persist for more than 24 hours. This invention provides a tool which directly records the MAP in the endomyocardium. Therefore, the subendocardial infarction could be diagnosed much earlier, and the position and area of the infarction could be determined more precisely.

Diagnosis For Dilated Cardiomyopathy:

Diagnosis of dilated cardiomyopathy still depends on the exclusion of all other causes. The MAP mapping is able to demonstrate the alteration of the cardiac myocytes function. Since the endomyocardium biopsy will only show the focal alteration, the mapping system demonstrates the diffuse abnormality of the cellular function, specially when the diffusive cell necrosis is present. Change of the amplitude, duration and/or dV/dt of MAP are the signs of the cellular dysfunction.

Diagnosis For Myocarditis:

Diagnosis of acute or chronic myocariditis is still lacking a "gold standard". Endomyocardial biopsy is more useful for diagnosis of diffuse myocariditis, but not focal myocariditis. Endomyocardial MAP mapping has a higher sensitivity for diagnosis of myocardiatis, specially focal myocariditis.

Diagnosis Of Atrium And Ventricular Arrhythmias:

Atrium and ventricular MAP mapping will be useful for diagnosis of intra-atrium and intra-ventricular conductance disturbances. This tool can also be used for determine the mechanisms of the atrial tachycardia (AT), atrial fibrilation (Af), atrial flutter (AF), ventricular tachycardia (VT), ventricular flutter (VF) and ventricular fibrillation (Vf), determine the turning point of the reentry, and guide for the ablation and drug testing.

Thus the invention opens a new era for the diagnosis of heart disease. Although it is an invasive procedure, the three-dimensional MAP mapping will be useful for diagnosis of many diseases with higher sensitivity and specificity, which could not be diagnosed use any existing technique, such as electrocardiograms (ECG), Echo, magnetic resonance imaging (MRI), EP tests or endocardium biopsy. There is no similar technique available. Sensitivity is defined as the ratio of the number of true positives divided by the sum of true positives and false negatives, and specificity is defined as the ratio of the number of true negatives divided by the sum of true negatives and false positives There are many advantages for this invention. For example, endomyocardial biopsy is the "gold standard" technique for diagnosis of rejection of heart transplantation. The invention could diagnose rejection much earlier without damaging the myocardium. The invention provides the tool for examining the myocardium in the whole heart at many points simultaneously (e.g. currently 64 points, although it is expressly contemplated that a useful and practical catheter will measure at 64 points and a time progresses even more points in later versions. Biopsy could only taking 4–5 pieces of the myocardium, and sometimes only the fibers without myocardium. The risk of arrhythmia and other complications are high for biopsy. Additionally, atrial rejection occurs earlier than in the ventricle, and a biopsy cannot be done in the atrium. Therefore, atrial MAP mapping will provide early diagnosis of rejection.

The advantages of the invention are better demonstrated by considering actual clinical data. To determine whether atrial conduction disturbance correlates with cardiac allograph rejection, we analyzed 249 12-lead—electrocardiograms (ECG), echocardiograms, hemodynamic para and endomyocardial biopsies (EMBs) from 137 patients with heart transplantation. Both heart signals, ptf-V1 and Ta-TcD, were significantly increased in ECG recordings from patients with severe, moderate, and even mild transplant rejection with p<0.0001. In 22 patients, serial analyses were performed during 5 weeks to 1 year follow-up. Significant increases of the ptf-V1and Ta-TcD were observed prior to positive histological findings, and these findings significantly correlated with severity of rejection. Increase of 0.030 mm-sec in ptf-V1 or 0.040 $s^{1/2}$ in Ta-TcD indicated cardiac rejection $\geq$1B with sensitivity of 88% and 83%, specificity of 85% and 77%, respectively. Increase of 0.040 mm-sec in ptf-V1 or 0.050 $s^{1/2}$ in Ta-TcD indicated rejection and an EMB grade $\geq$4a with sensitivity of 90% and 85%, and specificity of 88% and 80%, respectively. The lantern catheter could be used in a combination for laser ablation or as an adjunct to laser ablation. Selected ones of the wires and its electrode can be replaced by a fiber optic and an optical terminal end coupled to a laser. Since each electrode is insulated, one or more than one electrodes could be connected through a fiber optic with a laser for ablation. At the same time other electrodes could be used for the MAP mapping to simultaneously detect the injury induced by the ablation. The MAP mapping could also proceed immediately after ablation to identify the injury and to determine the effectiveness of the ablation.

Consider first some prior studies, which serve to highlight the advantage of the invention. Cardiac allograft rejection remains a major complication of heart transplantation and diagnosis is often difficult to make. To date, the most reliable method of rejection diagnosis is histological examination of EMB specimens. Because of the invasive procedure and inconvenience of EMB, particularly during the late follow-up period, various noninvasive markers of rejection have been actively investigated, included electrocardiography, echocardiography, magnetic resonance imaging, integrated ultrasonic backscatter analysis and antimyosin antibody imaging. Routine 12-lead ECG changes after orthotopic heart transplantation (OHT) have been thought to indicate acute rejection. These changes primarily consist of a decrease in the QRS complex voltage, arrhythmias, various degree of heart block, depression of ST segment and rightward shift in the frontal plane axis. Although a reduction in ECG voltage was formerly a reasonably specific marker for acute allograft rejection, the low sensitivity of this technique in patients receiving cyclosporine therapy negates its used. However, there remains a need for a simple and reproducible noninvasive method for the early prediction of cardiac allograft rejection.

These results demonstrated that the presence of atrial conduction disturbance correlates with allograft rejection and suggest that the ptf-V1, and Ta-TcD might be an adjunct to detect rejection and perhaps reduce the number of surveillance EMB.

In earlier studies, extensive rejection in the conduction system of a dog was found without significant rejection in the left ventricle. It was also observed that rejection was histologically more severe in the right ventricle than in the left ventricle, and much more severe in the atrial tissue than in the ventricular tissue of the transplanted dog hearts. Later, it was also demonstrated that intra-atrial and the AV conduction times were significantly prolonged with moderate to severe rejection, and the severity of atrium myocyte necrosis was significantly greater than in the ventricle. The greater degree of rejection in the atrium and conduction system and an early and severe involvement of the conduction system in the rejection process suggest the possibility of using atrial conduction disturbance as an early warning sign of allograft rejection.

Deviations from the normal pattern of the P wave in the presence of normal sinus rhythm, are caused by alteration in depolarization of the atrium. Analysis of the P wave in the ECG has been found to be a useful indicator of certain alteration of cardiac function. Alterations of the pif-V1 and the dispersion of the atrial repolarization (Ta-TD) are believed to represent intraatrial and interatrial conduction defects.

Based on these assumptions, the present study was designed to determine whether there was a relationship between ptf-V1 as well as Ta-TD and allograft rejection after heart transplantation. The significance of these measures was evaluated by correlation with the histological examination of EMB, echocardiography and hemodynamic parameters and determination of the sensitivity and specificity for identifying onset and severity of the cardiac allograft rejection.

Patients underwent orthotopic cardiac transplantation at our institute between 1993 and 1996 and having an ECG with EMB, echocardiogram and hemodynamic parameters were eligible for inclusion into the study. Patients with atrial arrhythmias, various kinds of heart block, permanent pacemakers and patients without a technically satisfactory 12 lead ECG taken during the acute event were excluded. Therefore, a total of 249 ECG recordings from 137 patients with concomitant EMB results, echocardiogram and hemodynamic parameters were available for analysis. The indication for transplantation included ischemic cardiomyopathy in 63, idiopathic cardiomyopathy in 59, complex congenital heart disease in five, hypertrophic cardiomyopathy in four, rheumatic heart disease in three, postpartum cardiomyopathy in two, and adramycin-induced cardiomyopathy in one. One hundred twenty-nine patients underwent orthotopic cardiac transplantation using a direct bicaval anastomosis technique, and the classic orthotopic operative technique of Lower and Shumway was only used in 8 other patients. All patients received conventional triple immunosuppression with cyclosporine, prednisone and either azithioprine or mycophenolate mofetil.

Using the method of Morris et.al., "P-Wave Analysis In Valvular Heart Disease," Circulation 1964;29:242–252, incorporated herein by reference, when normal sinus rhythm was present, ptf-V1 was measured from conventional 12 lead ECG recorded at a paper speed of 25 mm per second and a sensitivity of 1 mV per centimeter. Measurements of ptf V1 amplitude were made down to the nearest 0.25 mm and duration down to nearest 0.1 second. As shown in FIG. 1, the terminal force is defined as the product of the amplitude in millimeter and the duration in second of a possible negative terminal portion of the P wave. As the terminal portion may be a positive, isoelectric or negative, only the terminal portion with the negative deflection was calculated in our study. The positive or isoelectric terminal portions of the P wave were presented as the "zero" terminal force in this paper. To determine the duration or depth of the P terminal portion at least 3 (usually 5) P wave tracings were measured and averaged in order to avoid the effect of respiratory changes.

Figure 5A:
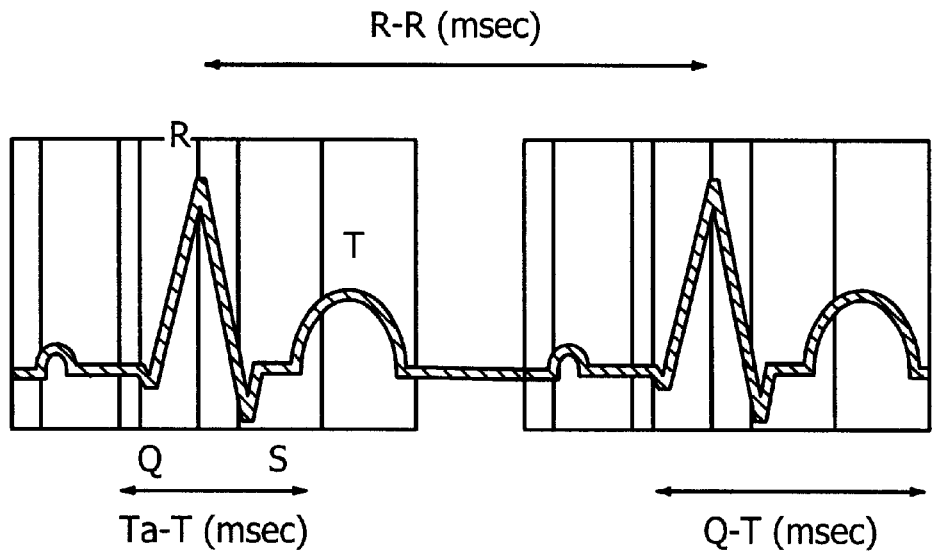
FIG. 5a is a diagrammatic wave diagram of a heart wave showing the schema of the ptf-V1, Ta-T and other measurements demonstrating the efficacy of using the invention to make an early detection of heart allograft rejection.

The isoelectric line was used for determining the Ta-T (from the end of the P wave to the beginning of the T wave), QRS, RR and QT interval. These time intervals are illustrated in FIG. 5a. The Ta-Tc and QTc dispersion were defined as the differences between minimal and maximal Ta-Tc intervals or QTc values, respectively, in any of the 12 leads, and the mean Ta-Tc and QTc dispersion were calculated for each patient. The rate-corrected QT and Ta-T interval were determined by using the Bazeft's formula, QTc (corrected QT) or Ta-Tc (corrected Ta-T in $s^{1/2}$)=QT or Ta-T (sec)/$(R-R)^{1/2}$ (sec)).

All measurements were performed by a single observer blind toward EMB, hemodynamic parameters and echocardiographic results in order to eliminate both interobserver variability and bias. All the internals were measured manually. In all cases the ECG taken on the date closest to the date of EMB was evaluated. In many cases the studies were done on the same day. For the entire group the time interval between these studies was 24–72 hours.

Cardiac allograft surveillance was achieved by means of regular transvenous right ventricular endomyocardial biopsy. Before hemodynamics were completed, right ventricular EMB specimens (usually three samples) were obtained with either the internal jugular or femoral vein approach. Specimens were fixed in 10% phosphate-buffered formalin and processed by routine paraffin embedding with an autotechricon tissue processor. Specimens were sectioned at 3 levels and stained with hemotoxylin and eosin. EMBs were performed once weekly ×4, biweekly ×2, biweekly ×2, monthly ×2 for the first six months. Thereafter, EMBs were obtained every 2 months ×3 for the first year; and at other times if there was clinical suspicion of rejection. Biopsies were histologically graded using the International Society of Heart and Lung Transplantation Classification (ISHLT). See, Billingham et.al. "*A Working Formulation For The Standardization Of Nomenclature In The Diagnosis Of Heart And Lung Rejection: Heart Rejection Study Group*". J Heart Transplant 1990;9:587–592.

Right heart catheterization was performed in the usual manner with a Swan-Ganz thermodilution catheter introduced through the internal jugular vein in conjunction with routine EMB in these cardiac transplant patients. Measurements of right atrial, right ventricular, pulmonary artery and pulmonary capillary wedge pressures were obtained. Cardiac output was measured in triplicate by the thermodilution method.

Parasternal long and short axis, and apical four and two chamber views were obtained during echocardiography. Left atrial dimension was determined from M-mode (parasternal long axis view), left ventricular mass, end-systolic and end-diastolic volume and ejection fraction were calculated by using a bi-plane ellipse method. Transmitral flow velocity was recorded by Doppler between the tips of the mitral leaflets from the apical four-chamber view. Echocardiographic signs suggestive of allograft rejection included decreased systolic function, increased in pericardial effusion and abnormal Doppler echocardiographic indices of diastolic dysfunctions.

All measurements are expressed as the mean±a standard deviation (SD) of the measured signal. The statistical evaluation was made by linear correlation analysis, one and two-way analysis of variance and multiple t test. ANOVA was used to test differences between changes observed in a subgroup of patients suffering from repeated rejection episodes with different rejection severity. Sensitivity (true-positives divided by true-positives plus false-negatives) and specificity (true-negatives divided by true-negatives plus false-positives) of rejection-induced changes in ECG parameters as an index of rejection were determined by constructing receiver operating characteristic (ROC) curve, for which various cutoff points may be selected from continuous scales of values to adjust the sensitivity and specificity of the test to confirm to clinical needs.

Figure 6A:
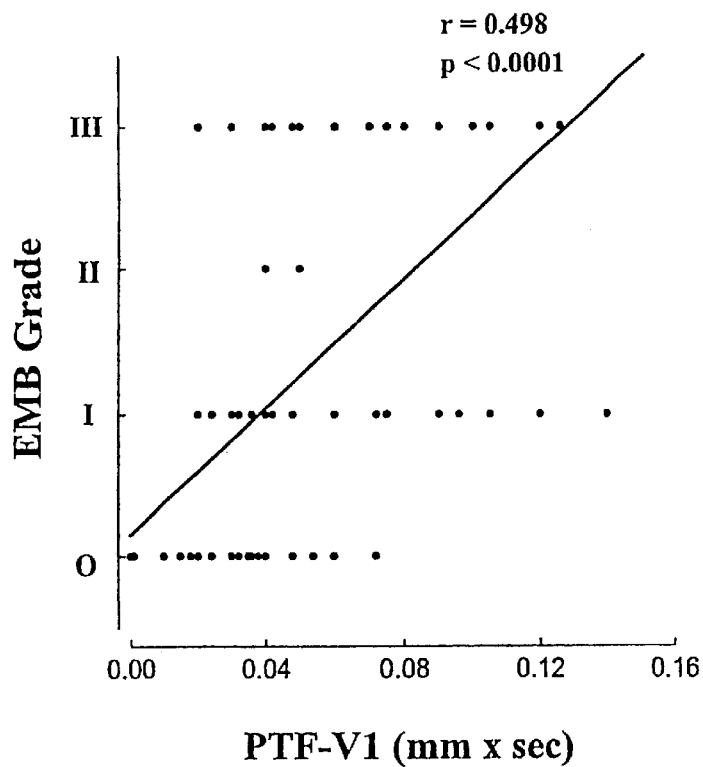
FIG. 6a shows the statistical correlation of the pif-V1 area and rejection grades from in heart transplant recipients.
Figure 6B:
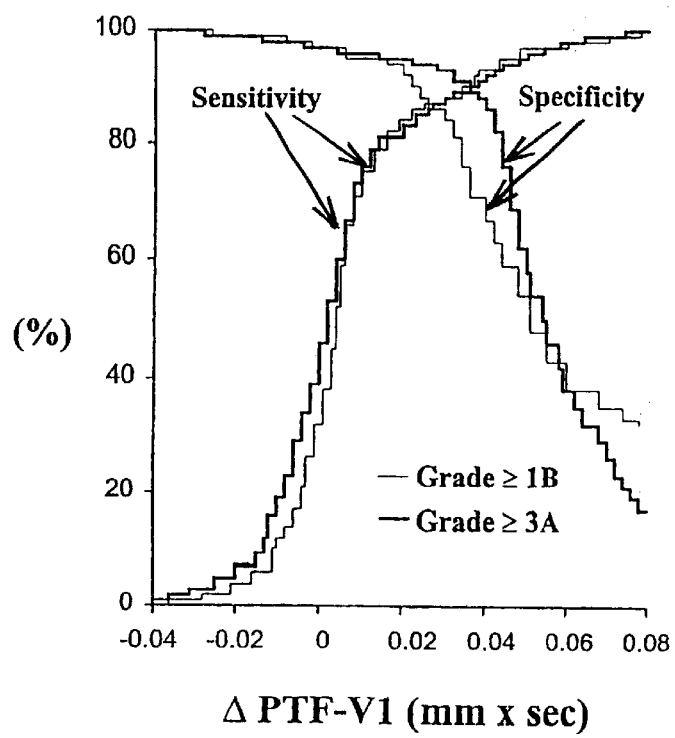
FIG. 6b shows the receiver operating curves (ROC) describing the sensitivity of the heart signal, ptf-V1, as index for cardiac allograph rejection. The curves are derived from 187 pairs of biopsy-controlled measurements, which were obtained from 137 heart transplant recipients. The X axis shows the change in ptf V1 area (mm-sec); and the y axis shows sensitivity/specificity (%). ROC curve using rejection grade $\geq$1B as diagnostic criterion and ROC curve using rejection grade $\geq$4a as diagnostic criterion are depicted.

The most consistent finding has been a stepwise but occasionally precipitous increase in the area of the ptf-V1 and the Ta-TcD. The heart signals which are measured are shown diagrammatically in FIG. 5a. Of the 249 EMBs performed in 137 heart transplant recipients corresponding to ptf-V1and Ta-TD measurements, 98 were classified as non-rejection (grade 0) and a total of 151 were classified as rejection, which included mild in 81, moderate in 6 and severe rejection in 64. For the group showing no rejection, the mean ptf-V1 was 0.029~0.012 mm-sec and in the group with histological evidence of rejection it was 0.055~0.028 mm. see ($p<0.001$). As shown in the graph of FIG. 5a, the heart signal ptf-V1 was most negative in the patients with severe rejection. The changes of ptf-V1 area was significantly correlated with the severity of the ISHLT grades ($r=0.498$, $p<0.0001$, as shown in FIG. 6a. These patients, however, seemingly have slower atrial conduction speeds, and this may be related to more generalized cellular damage, probably at the level of their ordinary working cells. The emergence of interatrial block may reflect the underlying pathologic state of the atrial myocardium in our patients, all of whom had rejection. Only 15 (from 7 patients) of 249 measurements had significant changes in ptf-V1 without any EMB rejection results. However, 5 of the 15 (from 3 patients) had abnormal hemodynamic and echocardiographic parameters and were found to require immunosuppressive treatment, suggesting the presence of humoral rejection.

Figure 5B:
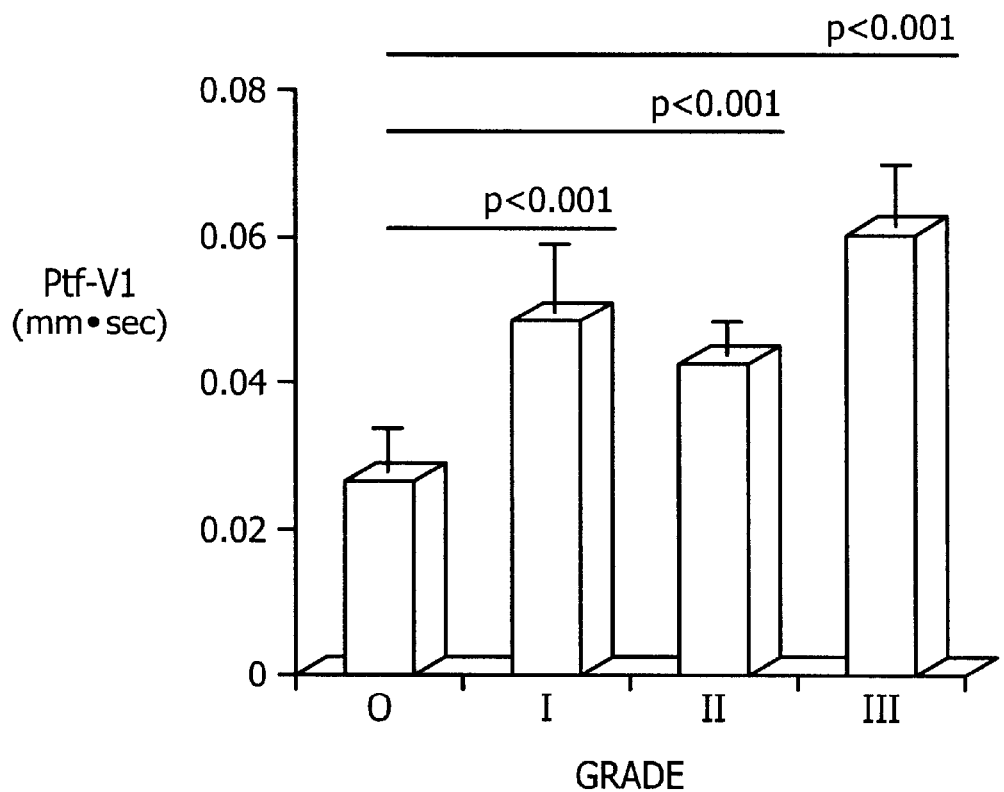
FIG. 5b is a bar graph that shows the mean ptf-V1 area versus histopathology in 137 heart transplant recipients in the study of FIG. 5a for different EMB grades.

FIG. 5b shows the sensitivity and the specificity of ptf-V1, changes an index for cardiac rejection. A histological rejection grade of either $\geq 1B$ or $\geq 4a$ was chosen as the criterion for construction of the receiver operating characteristic (ROC) curves. The points of interception of the sensitivity and specificity curves for rejection grades $\geq 1B$ and ≧4a were found at 0.053 mm. see and 0.063 mm-sec, respectively. An increase of the ptf-V1 0.030 mm-sec identified cardiac rejection ≧1B with sensitivity of 88% and specificity of 85%. An increase of the ptf-V1 0.040 mm. see identified cardiac rejection ≧4 a with sensitivity of 90% and specificity of 88%.

Abnormal ptf-V1 and temporal relation to results of serial EMB from 22 patients with mild, moderate or severe rejection and consecutive rejection-free measurements from 7 patients during 5 to 120 weeks follow-up. Increase of ptf-V1 was significantly more pronounced with moderate or severe rejection than with mild rejection in these patients who experienced both mild and more severe rejection (p<0.01). In patients with three or more consecutive rejection-free studies, the ptf-V1 was in the same range as that in the other patients in non-rejection group and yet remained unchanged in second, third or fourth measurements. Clearly discordant changes were rare. The statistically significant increase of the ptf-V1 concomitant with the histologically proved mild rejection suggests that the test remained adequate for detecting milder form of rejection. The increase of the ptf-V1 also appeared prior to the positive histological findings, upgrading or downgrading the rejection status in 11 out of 22 cases. These observations displayed that abnormal ptf-V1 was not only very satisfactory for assessing the severity of the rejection, and usually also reflects the onset of rejection and might be used for prediction of the changes of the rejection grades.

Figure 7A:
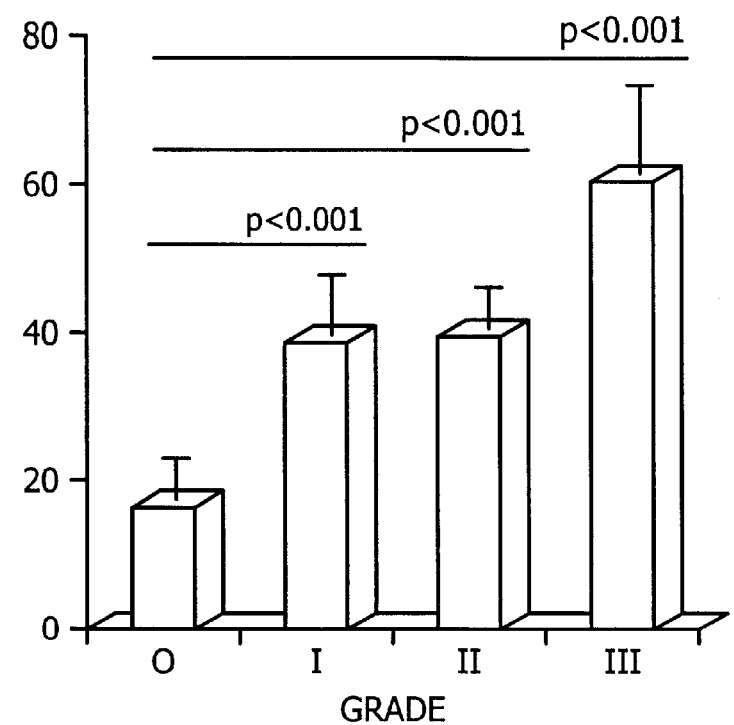
FIGS. 7a and 7b are bar graphs showing the mean heart signals, Ta-TD and Ta-TcD, respectively versus histopathology in 137 heart transplant recipients. The mean heart signals, Ta-T and Ta-Tc, dispersion was increased more than 2.8 folds in patients with rejection.
Figure 7B:
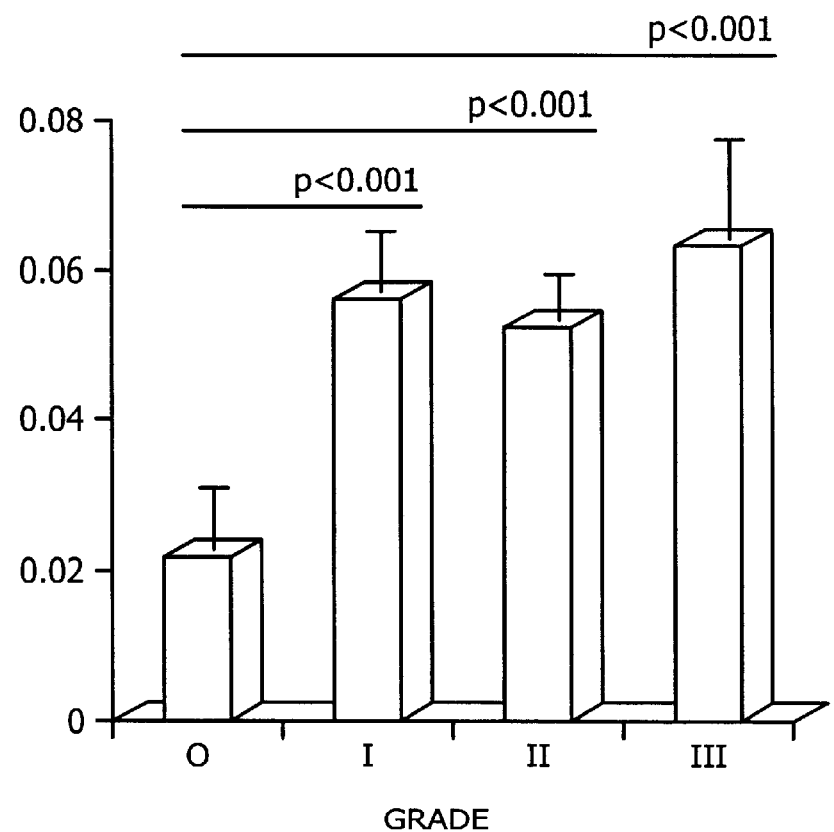

The mean Ta-TD and Ta-TcD in non-rejection patients was 16±10 msec and 0.021±0.09 $s^{1/2}$. The mean Ta-TD-and Ta-Tc greater for the patients with rejection (39±4 msec and 0.056±0.014 $s^{1/2}$, respectively) than without rejection (p<0.001). As shown in FIGS. 6a and 7bb, arranging the Ta-TD and Ta-TcD into subgroups according to the grade of rejection revealed significant difference in Ta-TD and Ta-TcD between the severe rejection group when compared with the group of moderate (60±27 msec and 0.063±0.015 $s^{1/2}$ vs. 40±6 msec and 0.052±0.006 $s^{1/2}$ p<0.001) or mild rejection (39±4 msec and 0.056±0.014 $s^{1/2}$, p<0.001).

Figure 8A:
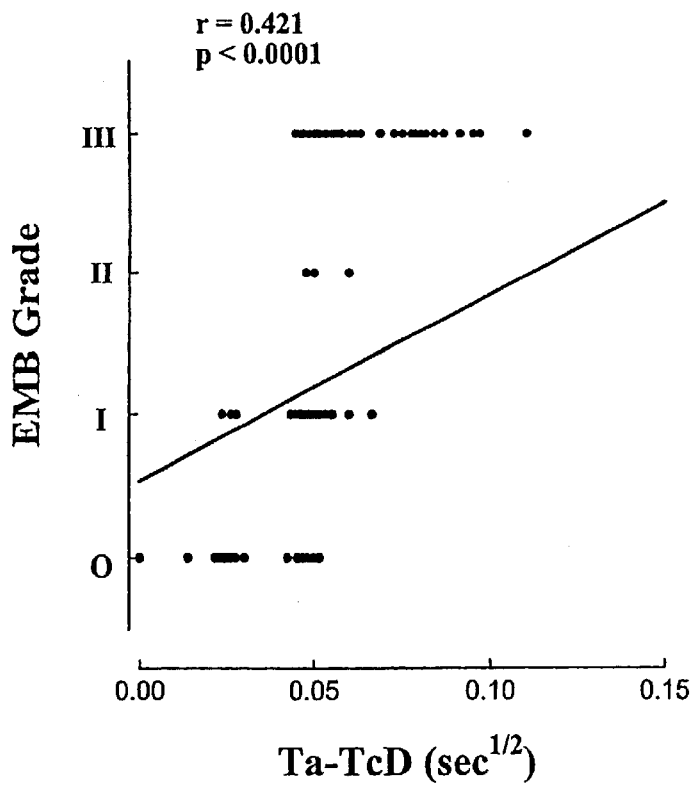
FIG. 8a shows the correlation of the heart signal, Ta-TcD, and rejection grades from 249 measurements in 137 heart transplant recipients. The Ta-TcD measurements were obtained at the same day of the endomyocarial biopsy (EMB) was performed.

The presence of repolarization changes of atrium was then correlated with the presence or absence of rejection seen in a right ventricular EMB. As shown in FIG. 8a, a significant linear correlation was documented between Ta-TcD and EMB grade. Of the seven patients showing absence of histological evidence for rejection at the time of abnormal ptf-V1, three of them were found to have humoral rejection also with increased Ta-TD and Ta-TcD. Therefore, abnormally prolonged Ta-TD and Ta-TcD recorded in these rejection patients reflect the inhomogeneity of local electrical activity related to a delayed and nonuniform anisotropic conduction through diseased atrial muscle.

Figure 8B:
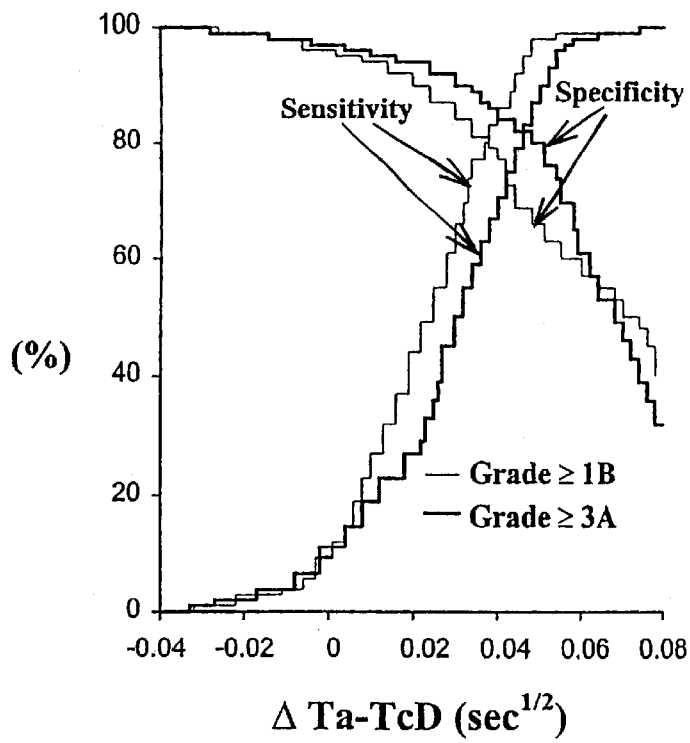
FIG. 8b shows the ROC curves describing the sensitivity of Ta-TD ($\geq$4a) and Ta-TcD ($\geq$1B) as index for cardiac allograft rejection. Curves are derived from 187 pairs of biopsy controlled measurements, which were obtained from 137 heart transplant recipients. The X axis is the change in ptf-V1 area (mm-sec); the y axis is the sensitivity/specificity (%).

FIG. 8b depicts the ROC curves describing the sensitivity and the specificity of Ta-TcD changes as an index for cardiac rejection. The points of interception of the sensitivity and specificity curves for rejection grades ≧1B and ≧4a were found at+0.038 $s^{1/2}$ and 0.046 $s^{1/2}$, respectively using these thresholds, the change of the Ta-TcD identified cardiac rejection. An increase of the Ta-TcD 0.040 $s^{1/2}$ identified cardiac rejection ≧1B with sensitivity of 83% and specificity of 77%. An increase of the Ta-TcD 0.050 $s^{1/2}$ identified cardiac rejection ≧4a with sensitivity of 85% and specificity of 80%. In comparison with ptf-V1, the slope of the ROC curve for the specificity of the Ta-TcD was significantly decreased (p<0.01), but the slope of the ROC curve for the sensitivity was not significantly different with ptf-V1.

Similar as ptf-V1, the changes of Ta-TD and Ta-TcD were also observed prior to the positive histological findings in 11 out of 22 patients during 5 weeks to 2 years follow-up, and represented the onset and also upgrade or downgrade of the severity of rejection.

Figure 9:
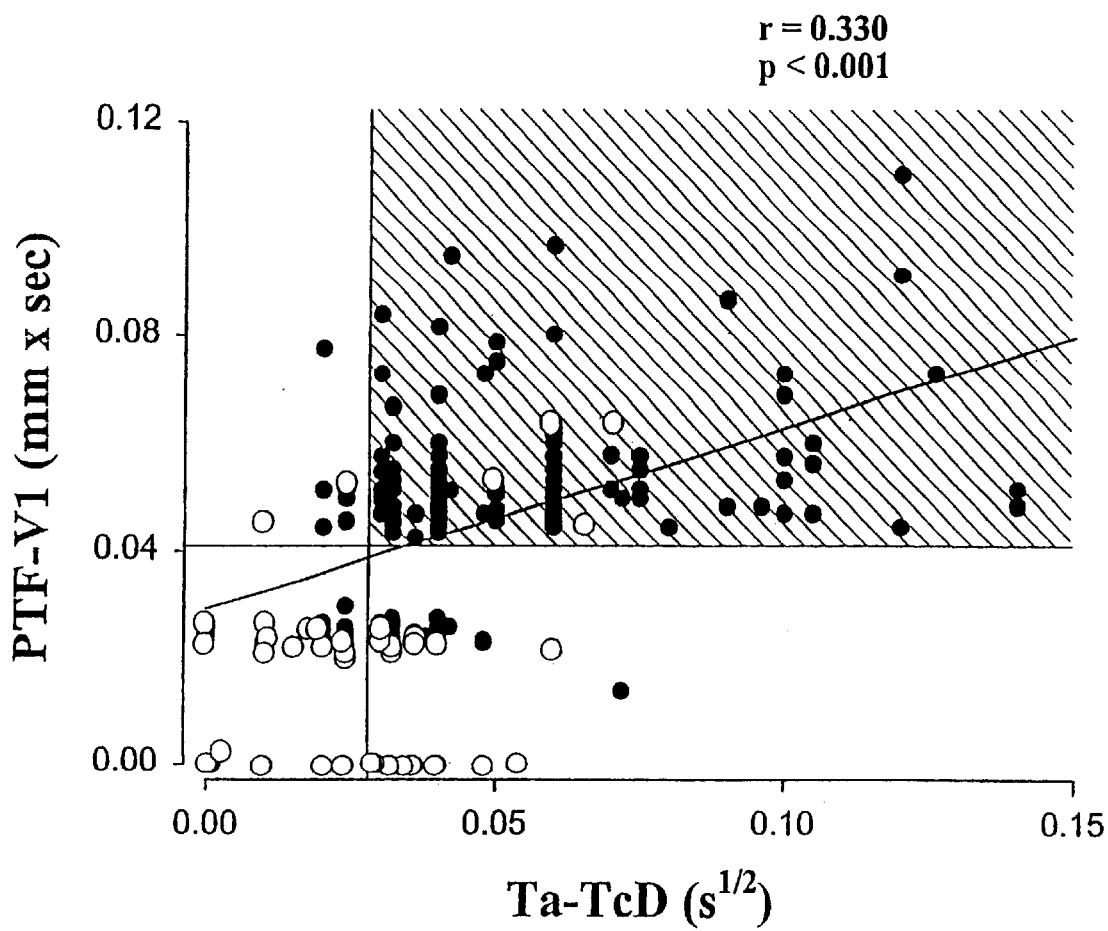
FIG. 9 shows the correlation of the changes of ptf-V1 area and Ta-TcD. The X axis is the changes of the ptf-V1 and the y axis is the changes of Ta-TcD from last preceding rejection-free measurements of the same patient (n=187, r=0.330, p<0.001, where n is the number of patients, r is the correlation with 1.0 being perfect correlation and 0 be no correlation, and p being a confidence measure of the statistical sampling with p<0.05 being regarded as statistically significant, i.e. more than 95% confidence level that the true value of the mean is within one standard deviation of the statistically measured value of the mean. Open circles represent non-rejection (grade 0), and filled circles represent rejection (EMB grade $\geq$1A). Using increment of 0.041 mm-sec of ptf-V1, combined with the increment of 0.030 $s^{1/2}$ of Ta-TcD as the index for identifying the allograft rejection, the specificity was significantly increased compared with only either one parameter was used (p<0.05).

FIG. 9 shows the change of the ptf-V1 from last preceding rejection-free measurements of the same patient was significantly correlated with the change of Ta-TcD (n=187, r=0.330, p<0.001). Using increment of 0.041 mm-sec of ptf-V1, combined with the increment of 0.030 $s^{1/2}$ of Ta-TcD as the index for identifying the allograft rejection, the specificity was significantly increased (p<0.05). In comparison with ptf-V1, Ta-TcD is a relatively nonspecific predictor of post operative rejection in patients undergoing heart transplantation.

Although the mean QT interval and QTc value were not different, the mean QT and QTc dispersions in patients with rejection (22.22±17.28 msec, 0.030±0.023 $s^{1/2}$, respectively) were significantly increased compared with that in patients without rejection (15.32±10.47 msec, 0.021±0.009 $s^{1/2}$, respectively, p<0.01). The significant increases of the QT and QTc dispersion were only observed in severe rejection, not in mild and moderate rejection. The correlation between the QTc dispersion and the histological rejection grades was still significant (r=0.27, p=0.026). However, the relation between the changes of QTc dispersion and the histological rejection grades was much weaker than the relation between the changes of ptf-V1 or Ta-TcD with the rejection grades. The thresholds of the changes of QT and QTc dispersion for identifying rejection ≧1B were +6 msec and +0.010 $s^{1/2}$, respectively, and for identifying rejection ≧4a were+10 msec and +0.020 $s^{1/2}$, respectively. The sensitivity of the QT and QTc dispersion identified cardiac rejection grade ≧4a was 74% and 72%, respectively, and the specificity was 76% and 77%, respectively. There is no significant difference in the mean QRS and RR intervals between rejection and non-rejection groups (p>0.05).

Table I lists the echocardiographic parameters and the hemodynamic variables for the patients with and without histological rejection. There were no significant differences in the left atrial dimension (LAD), mean right atrium pressure (RAP), mean pulmonary artery systolic (PASP) and diastolic pressures (PADP), and mean pulmonary capillary wedge pressure (PCWP) between two groups. Only the cardiac output (CO) and left ventricular ejection fraction (LVEF) were slightly reduced in rejection group (p=0.024 and p=0.045, respectively). However, no significant correlation could be found between the changes in any of the echocardiographic or hemodynamic parameters, with histological features of allograft rejection seen on EMB of the transplanted hearts.

When analyzing the effect of PCWP on ptfY1 and Ta-TD and Ta-TcD, we found no correlation between ECG data and the degree of pressure elevation in the capillary wedge (r=0.058, p>0.05, r=0.184, p>0.05, r=0.005, p>0.05, respectively). The correlation between LAD and ptf-V1 was poor (r=0.197, p>0.05). The Ta-TcD measurement failed to correlate with LAD and RAP as well (r=0.105 and r=0.136, respectively, p>0.05). Thus, echocardiographic enlargement of the left atrium was neither necessary for, nor associated with abnormal P terminal force or Ta-TcD. This suggests that the posterior rotation of the terminal P wave vector producing abnormal pif-V1is dependent more on interatrial conduction defect than on increased left atrium pressure and volume.

The above study demonstrates that patients with allograft rejection often have an abnormal ptf-V1. An abnormal ptf-V1 is usually associated with an increase of Ta-TcD. The significant correlation between the degree of ptf-V1and Ta-TcD increase, and the degree of rejection grade suggests that a cause and effect relationship may exist.

Changes in the pattern of atrial depolarization have long been recognized as reflecting anatomical or hemodynamic changes affecting the atria. The abnormal left atrium depolarization which caused abnormal ptf-V1 in our cases may be attributed to a number of factors; these include alterations of left atrial volume and pressure, as well as intrinsic atrial pathology such as interatrial conduction defect.

Previous reports have shown that ptf-V1 correlates significantly with the left atrial dimension as measured by echocardiography in various cardiac diseases. However, less than half of our patients had left atrial dimension increase, and there was no significant difference between the rejection and non-rejection groups. Other studies indicate that the mean left atrial pressure and its serial changes, are closely correlated with the ptf-V1. Hemodynamic changes after transplantation could affect the morphology of the donor atrial P wave. In our study, comparison of ptf-V1 with PCWP or PADP measurements, yielded a poor correlation. Left atrial abnormality is a frequent finding in systemic hypertension and may occur even in the absence of cardiac enlargement and coronary artery disease. It has been suggested that these changes might reflect an interference in atrial conduction. Hypertension develops in majority of patients after heart transplant due to the use of cyclosporine. Patients in our group all were immunosuppressed with cyclosporine. Even though half of our studying patients developed hypertension, our data failed to show a correlation of increased ptf-V1 with left atrial size/pressure, or with systemic hypertension.

The prominent negative P deflection in Lead V1 caused by a posterior rotation of the left atrial vector in the horizontal plane is well known. A transplanted heart is commonly rotated on its long axis after aorta and pulmonary artery anastomosis have been completed, and this position is maintained because of the large mediastinal space that remains after the diseased heart has been excised. Posterior displacement of the atrial vector in acute allograft rejection may also be due to left atrial distention secondary to left ventricular failure. The presence of a measurable ptf-V1 may actually reflect this abnormal cardiac position. However, it is unlikely that all of the above factors play a significant role in the genesis of the P-wave abnormalities in our patients.

The factor which is more likely to contribute to P wave abnormalities in cardiac allograft rejection is intra- and/or interatrial conduction defects. Such a factor may explain the presence of abnormal P wave in cases where there is neither radiological and echocardiographic evidence of left atrial enlargement or hemodynamic evidence of left atrial pressure overload. In a recent electrophysiologic study, it has been suggested that an interatrial conduction defect may be the underlying cause for the ECG pattern of abnormal ptf-V1 (left atrial enlargement). Some practitioners have placed sutures around certain strategic points on the internodal and interatrial pathways and were able to change the form of the P wave indicating the production of an abnormal depolarization wave in atrial conduction. Others have arrived at a similar conclusion, namely, that damage to the conduction paths in the atrium might be expected to cause significant change in P wave configuration or polarity even in the absence of a significant shift in the pacemaker. Moreover, the mid-matrial cuff and bicaval anastomosis technique involves anastomosis of both or one donor atria to the recipient, leaving a cuff of the recipient's atria and resulting in an atrial suture line with possible of electrical conduction disturbance. Therefore, the presence of abnormal ptf-V1 in heart transplant patients with normal size atria and pulmonary capillary wedge pressure (PCWP) strongly suggests the existence of atrial conduction disease. The emergence of interatrial block may reflect the underlying pathologic state of the atrium conduction tissue and myocardium in our patients. Increased ptf-V1 is, however, occasionally seen in routing electrocardiogram of apparently healthy individuals, possibly this finding in individuals without symptoms or signs of heart disease is due to a clinically unimportant abnormality of the interatrial conduction.

In view of these considerations and findings of a correlation between ptf-V1 and rejection grade, as well as the demonstration of an increased incidence of atrial fibrillation in rejection group, it seems reasonable to conclude that an abnormal ptf-V1 is causally related to the atrial conduction disturbance in patients with allograft rejection.

The subject of duration of electrical activity in the atrium has had renewed attention. Analysis of the terminal portion of the atrial complex and the total duration of the atrial activity is of theoretical as well as practical interest, especially in the relation to atrial arrhythmias and atrial conduction disturbance. According to the current theory of the Ta wave, the area subtended by the P wave is equal in size and opposite in direction to the Ta wave, but is usually obscured by the after coming—ventricular complex and extend well into the ST segment even T wave. Therefore study of the Ta wave is difficult, because most of it is buried in the deflection resulting from ventricular activity. Under normal conditions, the only visible part of the atrial recovery wave in ECG is the PQ segment. Previous studies have shown that the secondary alteration of repolarization which primarily effect the depolarization have been described in hypertrophy and dilatation of the atria and interatrial block. In the disclosed study, duration of the atrial repolarization is measured by the Ta-T interval from the end of the P wave to the beginning of the T wave corresponding to the ventricular IT interval. The duration of the atrial repolarization wave has been reported to be considerably longer than that of the P wave. Others have showed the duration of interval from the onset of the P wave to the end of the atrial repolarization wave to be 2.7 to 4 times the P wave duration. Other investigators reported atrial repolarization wave lasting up to 600 ms after the onset of the P wave. The Ta-T interval observed in this study is in this range. Abnormalities of the Ta wave might give us an important clue to find the existence of disease in the atria.

Dispersion of refractoriness of atrial tissue may predict postoperative atrial fibrillations. The mechanism responsible for the increased dispersion of refractoriness might be the nonuniform state of the diseased atrial cell. During the allograft rejection process, the injury of myocardial cell membrane, which may affect phase 2 or 3 of the action potential, and the derangement of myocardial fibers in the conduction system may be responsible for the decrement and/or inhomogeneous conduction. As the left atrial conduction velocity decreases, the asynchromy between the right and left atria events become apparent. This is particularly well seen in Ta-T dispersion. Changes in depolarization properties of the atrial myocardium due either to local features such as that occur in acute rejection or by general effects of drugs, or the autonomic nerve system could also increase atrial conduction inhomogeneity.

In this study, a significant prolonged Ta-TcD during cardiac allograft rejection was found. Moreover, it seems to reflect the severity of the rejection process and appeared to be a more sensitive, but a less specific measurement of rejection than ptf-V1. The change in Ta-TcD suggests a greater rejection rate in the atrium versus the ventricular tissues. This also indicated that the prolonged and nonuniform refractoriness found in patients with rejection reflects intrinsic atrial disease.

Allograft rejection in patients treated with cyclosporine is almost always clinically silent. Even seemingly advanced histological stages of the rejection with striking myocyte necrosis are not always associated with clinical signs or symptoms. Significant increases of ptf-V1 and Ta-TcD were found to appear earlier than histological findings, and the increments were significantly correlated with severity of myocyte damage. These results suggest these parameters might be used for noninvasive prediction of rejection, which could reduce the number of surveillance EMB during the late follow-up period. Sensitivity and specificity were greatly increased by measuring ptf-V1 with Ta-TcD. Measurements of pif-V1 and Ta-TcD also approve to detect mild rejection and possibly immoral rejection. This would enhance the clinical verifying of this form of rejection detection.

In this study, histological evidence of cardiac rejection was associated with an abnormal ptf-V1 and Ta-TD. These changes reflect atrial conduction defects that accompany the rejection process. Because the ptf-V1 area and Ta-TcD increases were occurred prior to the histopathological findings and significantly correlated with the severity of the rejection, these results demonstrate the feasibility of using these parameters to predict the onset of the rejection episode and estimate the severity of the rejection. Our results suggest that measurements of ptf-V1 and Ta-TcD may be a useful adjunct to EMB for surveillance of rejection in the long term management of cyclosporine treated heart transplant.

Figure 10A:
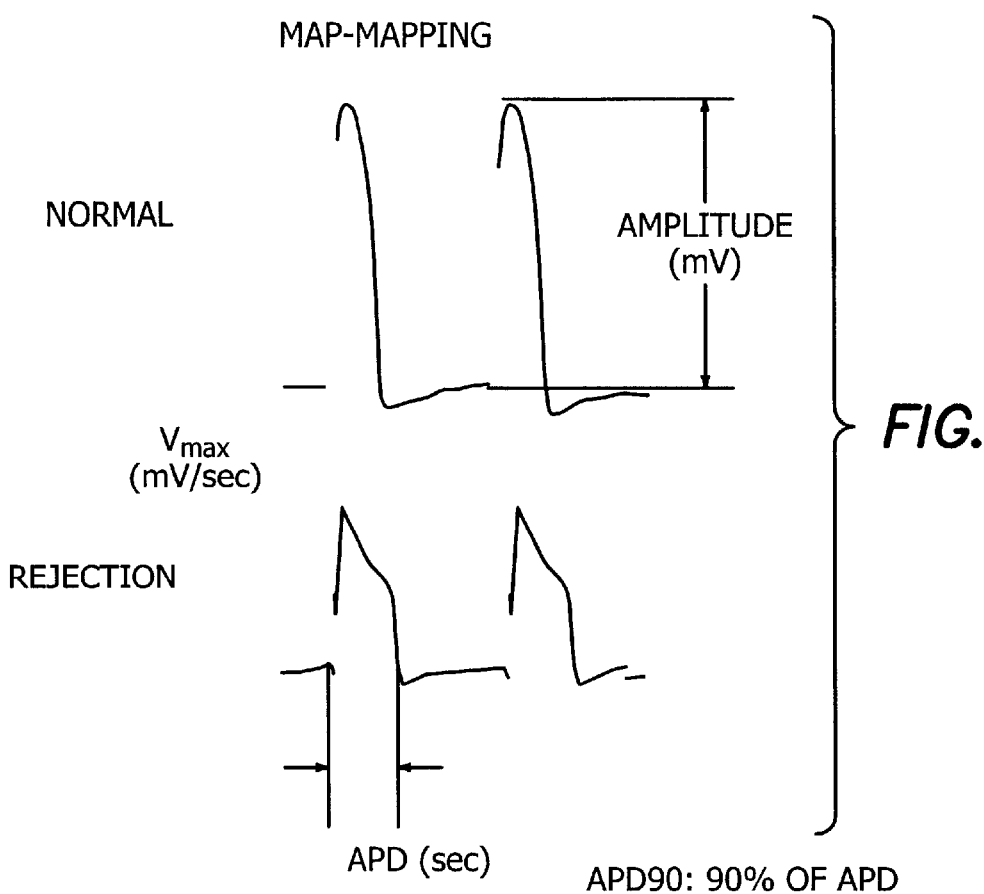
FIG. 10a is a time graph of a MAP mapping showing the waveform in the upper portion of the Figure from a normal heart or a heart transplant which is accepted. The lower portion of the Figures shows a time graph of a MAP mapping signal of a heart transplant which is being rejected. The width of the signal is denoted as the signal APD and 90% of the total width is denoted as APD90.
Figure 10B:
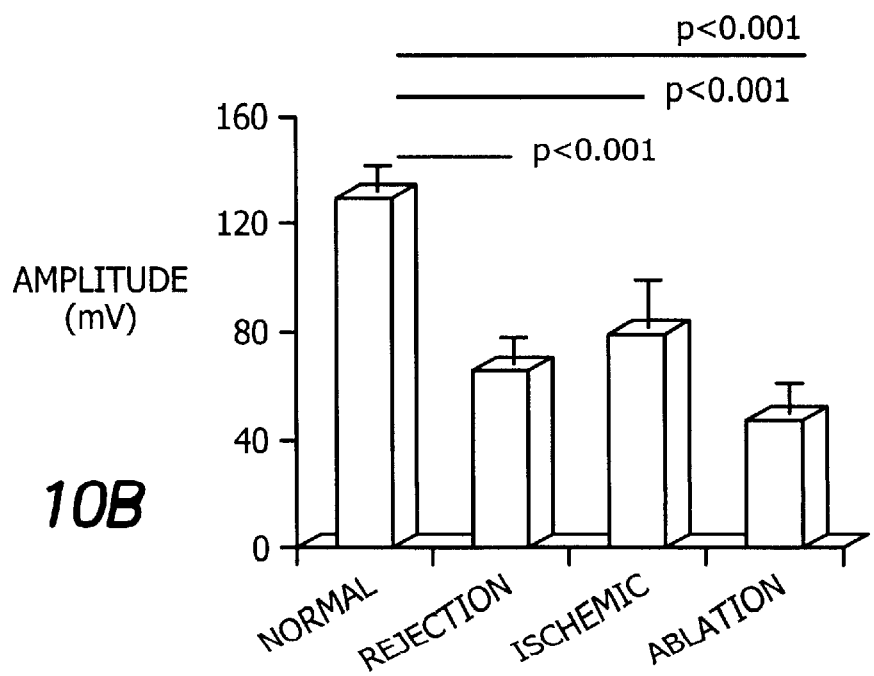
FIG. 10b is a bar graph of the MAP mapping amplitudes for a normal, rejected, ischemic and ablated heart transplant.
Figure 11A:
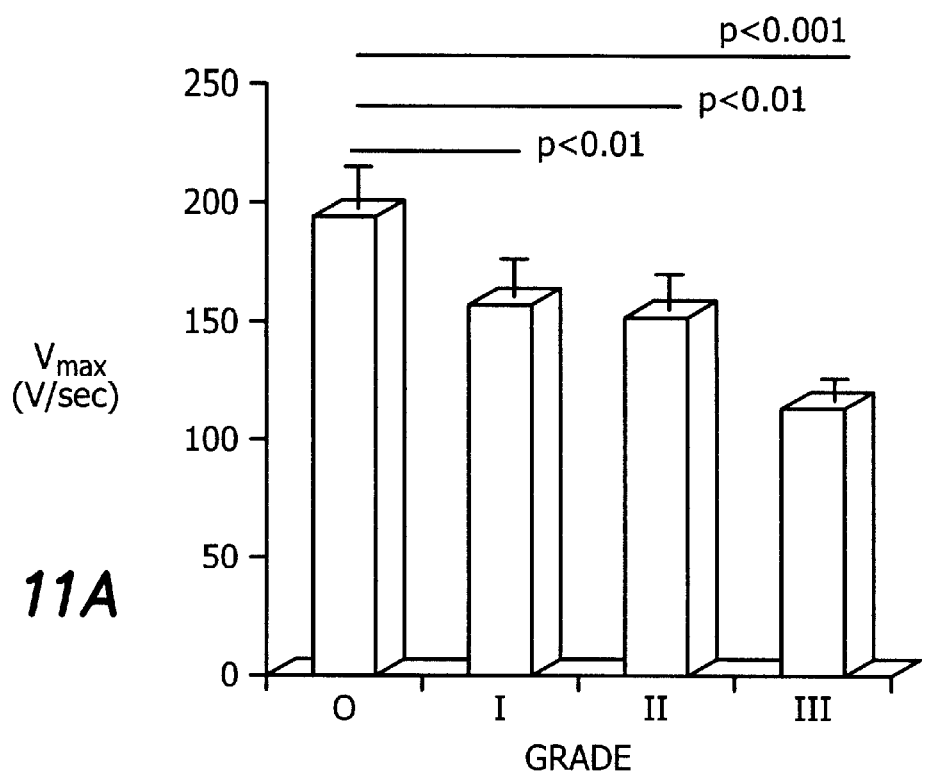
FIG. 11a is a bar graph of the maximum upstroke velocity (Vmax) of the MAP for four EMB grades.
Figure 11B:
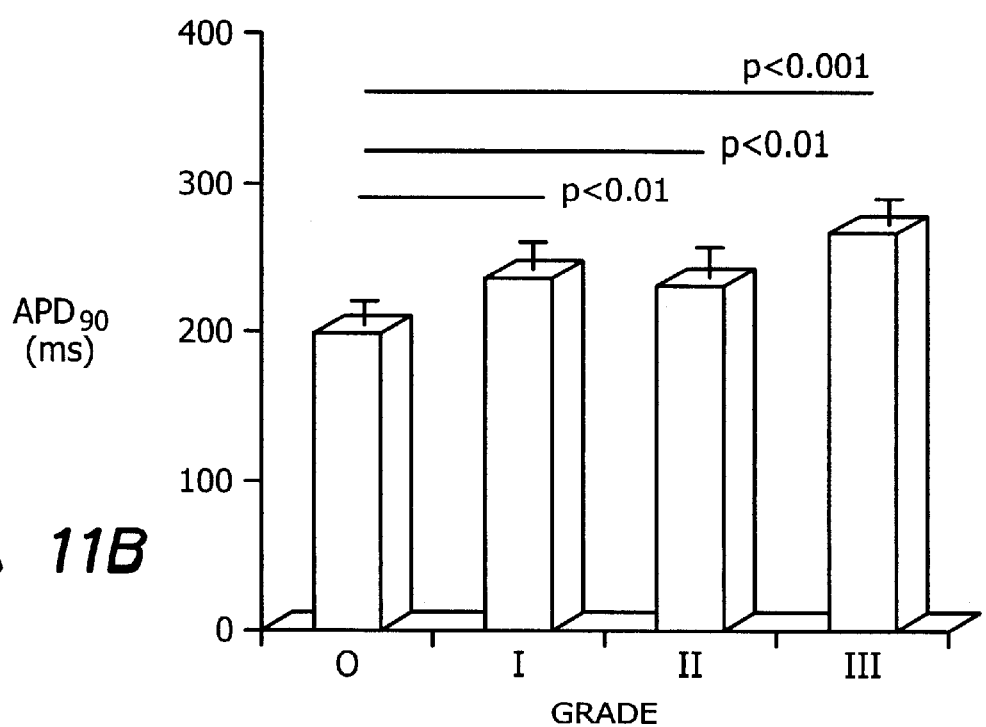
FIG. 11b is a bar graph of the action potential duration 90 (APD90) for four EMB grades.

FIGS. 10a and 10b illustrate the usefulness of using the amplitude and signal width of a MAP mapping to detect heart damage or allograph rejection. FIG. 10a shows the maximum upstroke velocity (Vmax) of the MAP in the lower graph on the leading edge of the signal, which Vmax signal is also useful to determine myocardial injury. The statistical results of the use of amplitude to obtain detection of myocardial injury is illustrated for different types of myocardial injury in FIG. 10b. A different MAP mapping amplitude will be statitically significant at different levels depending on the type of myocardial injury. FIGS. 11a and 11b illustrate the statistically significant levels of the Vmax and APD90 signals respectively as defined in connection with FIG. 5a for different grades of myocardial injury, which levels again depend on the grade of myocardial injury.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for three-dimensional interior mapping of endomyocardial monophasic action potential (MAP) of endomycardial tissue comprising:
   a catheter with a distal and proximal end;
   a wire basket disposed on said distal end of said catheter;
   a plurality of electrodes forming an array of separated electrodes carried by said wire basket, said wire basket self-expandable by reason of resiliency of said wire basket to a size and stiffness sufficient to cause said electrodes to make intimate contact with said endomycardial tissue with point contact pressure at each electrode; and
   a flexible cable disposed in said catheter electrically coupling said plurality of electrodes to said proximal end of said catheter.

2. The apparatus of claim 1 further comprising an electrophysiological analyzer coupled to said cable to record data from each of said plurality of electrodes and to analyze said data to generate a three-dimensional endomyocardium mapping of endomyocardial monophasic action potential from said plurality of electrodes.

3. A method of determining the myocardium injury/electrical-pathophysiology of cardiac myocytes comprising:
   providing a catheter having with a distal and proximal end, and a wire basket disposed on said distal end of said catheter with a plurality of at least 64Ag/AgCl plated electrodes carried by said basket, having a flexible cable disposed in said catheter electrically coupling said plurality of electrodes to said proximal end of said catheter, and a sheath temporarily disposed over said basket to retain said basket in a collapsed configuration;
   disposing said catheter in a heart chamber to be mapped,
   telescopically removing said sheath from said basket to allow said basket to self-expand in said heart chamber, said basket being self-expandable by reason of resiliency of said basket to a size and stiffness sufficient to cause said electrodes to make intimate contact with said endomycardial tissue; and recording and electrophysiologically analyzing a data signal from each of said plurality of electrodes to generate a three-dimensional endomyocardium mapping of endomyocardial monophasic action potential from said plurality of electrodes.

4. The method of claim 3 where recording and electrophysiologically analyzing said data signal from each of said plurality of electrodes comprises recording and electrophysiologically analyzing a maximum amplitude of the action potential (Amax) and the dispersion of the amplitude of the action potential (AP) from each of said plurality of electrodes to determine myocardium injury.

5. The method of claim 3 where recording and electrophysiologically analyzing said data signal from each of said plurality of electrodes comprises recording and electrophysiologically analyzing an action potential duration and dispersion of the action potential duration from each of said plurality of electrodes to determine myocardium injury.

6. The method of claim 3 where recording and electrophysiologically analyzing said data signal from each of said plurality of electrodes comprises recording and electrophysiologically analyzing a maximum diastolic potential from each of said plurality of electrodes to determine myocardium injury.

7. The method of claim 3 where recording and electrophysiologically analyzing said data signal from each of said plurality of electrodes comprises recording and electrophysiologically analyzing a maximum upstroke velocity (Vmax) of the MAP from each of said plurality of electrodes to determine myocardial injury.

8. The method of claim 3 where recording and electrophysiologically analyzing said data signal from each of said plurality of electrodes comprises recording and electrophysiologically analyzing a P wave in EKG lead V1 (ptf-V1) signal from each of said plurality of electrodes to determine myocardium injury.

9. The method of claim 3 where recording and electrophysiologically analyzing said data signal from each of said plurality of electrodes comprises recording and electrophysiologically analyzing a dispersion of the atrial repolarization (Ta-TcD) signal from each of said plurality of electrodes to determine myocardium injury.

10. The method of claim 9 where recording and electrophysiologically analyzing said data signal from each of said plurality of electrodes comprises recording and electrophysiologically analyzing a P wave in EKG lead V1 (ptf-V1) signal from each of said plurality of electrodes to determine myocardium injury.

* * * * *